United States Patent
Karan et al.

(10) Patent No.: US 11,988,672 B2
(45) Date of Patent: May 21, 2024

(54) CCL24 AS A DIAGNOSTIC AND THERAPEUTIC TARGET FOR BREAST CANCER

(71) Applicant: University of South Carolina, Columbia, SC (US)

(72) Inventors: Dev Karan, Cayce, SC (US); Seema Dubey, Cayce, SC (US)

(73) Assignee: University of South Carolina, Columbia, SC (US)

(*) Notice: Subject to any disclaimer, the term of this patent is extended or adjusted under 35 U.S.C. 154(b) by 54 days.

(21) Appl. No.: 17/102,633

(22) Filed: Nov. 24, 2020

(65) Prior Publication Data

US 2021/0208161 A1   Jul. 8, 2021

Related U.S. Application Data

(60) Provisional application No. 62/940,396, filed on Nov. 26, 2019.

(51) Int. Cl.
*G01N 33/68* (2006.01)
*C07K 16/24* (2006.01)
*G01N 33/50* (2006.01)
*G01N 33/574* (2006.01)
*A61K 39/00* (2006.01)

(52) U.S. Cl.
CPC ......... *G01N 33/6863* (2013.01); *C07K 16/24* (2013.01); *G01N 33/5044* (2013.01); *G01N 33/5047* (2013.01); *A61K 2039/505* (2013.01); *C07K 2317/76* (2013.01); *G01N 33/57415* (2013.01); *G01N 2333/521* (2013.01)

(58) Field of Classification Search
None
See application file for complete search history.

(56) References Cited

PUBLICATIONS

Tang (2013, Cancer Letters 332:3-10).*
Williams et al. (2016, npj Breast Cancer 2:15025; doi:10.1038/npjbcancer.2015.25; published online Jan. 20, 2016).*
CCL24 Gene, https://www.genecards.org/cgi-bin/carddisp.pl?gene=CCL24; accessed Sep. 16, 2022.*

* cited by examiner

Primary Examiner — Elizabeth C. Kemmerer
(74) Attorney, Agent, or Firm — Burr & Forman LLP; Douglas L. Lineberry (57) ABSTRACT

Using expression of CC chemokine ligand (CCL24) to serve as an identification of a potential deriver of metastatic cancers and methods of detecting the presence of CCL24 to serve as a breast cancer diagnosis tool.

13 Claims, 5 Drawing Sheets

Specification includes a Sequence Listing.

CCL24 AS A DIAGNOSTIC AND THERAPEUTIC TARGET FOR BREAST CANCER

TECHNICAL FIELD

The present invention relates to use of the CC chemokine ligand (CCL24) molecule as a diagnostic and therapeutic target for breast cancer.

BACKGROUND

Breast cancer is the most common cancer in women worldwide, and the second leading cause of cancer-related deaths among women in the United States. It is estimated that there are more than 3.5 million women living in the United States with a history of invasive breast cancer, and additional 246,660 new cases will be diagnosed with expecting deaths of 40,450 in 2016. An estimated 90% of deaths due to breast cancer are a result of metastatic disease, whether cancer was metastatic at diagnosis or a metastatic recurrence.

Of all the subtypes of breast cancer, triple negative breast cancer (TNBC) is the most aggressive cancer, and is characterized due to lack of three receptor proteins: estrogen receptor (ER), progesterone receptor (PR), and human epidermal growth factor receptor 2 (HER2). Unfortunately, TNBC is more prevalent in African American women, and strikes at younger age patients.

Current breast cancer treatments include surgery, radiation therapy, chemotherapy, or hormonal therapy, and lately some improved therapies targeting specific molecules in breast cancer. Although some changes in the treatment approach improve quality of life, they do not change the overall mortality rates. Therefore, identifying new mechanisms that control the development and progression of breast cancer is of great significance to facilitate the design of new therapeutics aimed at inhibiting breast cancer metastasis and reducing mortality.

The development and progression of tumor cells is driven by the molecular changes accumulated within cells over time. These developing tumor cells are in continuous equilibrium with the immunologic targets within the tumor microenvironment, eventually evading the immune system. There are multiple optional treatment for breast cancer. However, the treatment eventually fails and disease recurrence remains a significant clinical challenge. Therefore, an unmet critical need is to identify and characterize novel molecules to help better understand the development and progression of metastatic breast cancer, so they can be used for targeted therapy.

Accordingly, it is an object of the present disclosure to determine if molecular expression of CC chemokine ligand (CCL24) may serve as an identification of a potential deriver of metastatic breast cancer. If successful, potential oncogenic function of CCL24 may help to revolutionize treatment regimens eliminating mortality associated with metastatic breast cancer.

SUMMARY

In a first embodiment, the current disclosure provides a breast cancer detection method. The method includes analyzing a subject for a tumor microenvironment, analyzing immune suppression events in the tumor microenvironment, and determining the amount of at least one chemokine in the tumor microenvironment. Further, the chemokine comprises CCL24. Still yet, the method comprises analyzing basal-like breast cancer cells. Still further, the method includes analyzing for polarization of at least one tumor associated microphage. Further yet, the method includes analyzing the tumor microenvironment for immune suppressor cells. Yet further, the immune suppressor cells comprise CCR3 expressing immune suppressor cells. Again still, the method includes analyzing for defecting of effector function for cytotoxic immune cells.

In an alternative embodiment, a method is provided for cancer detection. The method includes analyzing a subject for a tumor microenvironment, analyzing immune suppression events in the tumor microenvironment, and determining the presence of a serum-based biomarker. Further, the serum based biomarker comprises a chemokine. Still yet, the chemokine comprises CCL24. Yet still, the cancer being detected comprises breast cancer. Further, the method includes analyzing for polarization of at least one tumor associated microphage. Still again, the method includes analyzing the tumor microenvironment for immune suppressor cells. Still yet, the immune suppressor cells comprise CCR3 expressing immune suppressor cells. Again yet, the method includes analyzing for defecting of effector function for cytotoxic immune cells.

In a still further environment, a method is provided for inhibiting modulation of immunosuppressor cells in a tumor microenvironment comprising inhibiting migration and metastasis of breast cancer cells via inhibition of CCL24 formation through knockdown.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present disclosure will be obtained by reference to the following detailed description that sets forth illustrative embodiments, in which the principles of the disclosure may be utilized, and the accompanying drawings of which.

The figures herein are for illustrative purposes only and are not necessarily drawn to scale.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF A PREFERRED EMBODIMENT

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further embodiment includes from the one particular value and/or to the other particular value. The recitation of numerical ranges by endpoints includes all numbers and fractions subsumed within the respective ranges, as well as the recited endpoints. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the singular forms "a", "an", and "the" include both singular and plural referents unless the context clearly dictates otherwise.

As used herein, "about," "approximately," "substantially," and the like, when used in connection with a measurable variable such as a parameter, an amount, a temporal duration, and the like, are meant to encompass variations of and from the specified value including those within experimental error (which can be determined by e.g. given data set, art accepted standard, and/or with e.g. a given confidence interval (e.g. 90%, 95%, or more confidence interval from the mean), such as variations of +/−10% or less, +/−5% or less, +/−1% or less, and +/−0.1% or less of and from the specified value, insofar such variations are appropriate to perform in the disclosure. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the singular forms "a", "an", and "the" include both singular and plural referents unless the context clearly dictates otherwise.

As used herein, "about," "approximately," "substantially," and the like, when used in connection with a measurable variable such as a parameter, an amount, a temporal duration, and the like, are meant to encompass variations of and from the specified value including those within experimental error (which can be determined by e.g. given data set, art accepted standard, and/or with e.g. a given confidence interval (e.g. 90%, 95%, or more confidence interval from the mean), such as variations of +/−10% or less, +/−5% or less, +/−1% or less, and +/−0.1% or less of and from the specified value, insofar such variations are appropriate to perform in the disclosure. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed by the term "subject."

As used interchangeably herein, the terms "sufficient" and "effective," can refer to an amount (e.g. mass, volume, dosage, concentration, and/or time period) needed to achieve one or more desired and/or stated result(s). For example, a therapeutically effective amount refers to an amount needed to achieve one or more therapeutic effects.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as cancer and/or indirect radiation damage. The effect can be therapeutic in terms of a partial or complete cure of a disease, condition, symptom or adverse effect attributed to the disease, disorder, or condition. The term "treatment" as used herein covers any treatment of cancer and/or indirect radiation damage, in a subject, particularly a human and/or companion animal, and can include any one or more of the following: (a) preventing the disease or damage from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, the terms "weight percent," "wt %," and "wt. %," which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt % values the specified components in the disclosed composition or formulation are equal to 100.

As used herein, "water-soluble", generally means at least about 10 g of a substance is soluble in 1 L of water, i.e., at neutral pH, at 25° C.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present disclosure. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the disclosure. For example, in the appended claims, any of the claimed embodiments can be used in any combination.

All patents, patent applications, published applications, and publications, databases, websites and other published materials cited herein are hereby incorporated by reference to the same extent as though each individual publication, published patent document, or patent application was specifically and individually indicated as being incorporated by reference.

Tumor microenvironment (TME) is considered a prime factor for homing, nurturing, and driving the development and progression of cancer. TME is complex and constitutes multiple cell types including immune cells. There is a group of proteins called 'chemokines', which facilitates lymphocyte trafficking under specific conditions and angiogenesis inducing inflammation supporting tumorigenesis and metastasis of cancer. The current disclosure identifies a novel molecule associated with the TME at the interplay of oncology and immunology. The current disclosure has observed a significantly higher level of CCL24 in basal like breast cancer cells. Therefore, the current disclosure posits that the chemokine CCL24 drives the progression of aggressive breast cancer leading to metastasis and detection of same can lead to early diagnosis of breast cancer.

The current disclosure seeks to determine the molecular function of chemokine ligand CCL24 in breast cancer, and to investigate if CCL24 serves as a potential deriver of metastatic breast cancer, addressing the overarching challenges of identifying novel determinants of breast cancer, and its potential as a therapeutic target in reducing/eliminating mortality due to breast cancer.

CCL24 also known as myeloid progenitor inhibitory factor 2 (MPIF-2) or eosinophil chemotactic protein 2 (eotaxin-2) is a protein that in humans is encoded by the CCL24 gene. Chemokines are small, cell secreted proteins that primarily regulate leukocyte trafficking in homeostatic conditions and during specific immune responses. Chemokines guide the migration and adhesion of leukocytes and influence diverse physiological functions including cell proliferation, angiogenesis, inflammation, tumorigenesis and metastasis. Chemokines are associated with the establishment of pro-tumor microenvironment stimulating tumor cell progression and metastasis.

In fact, chemokines constitute a large family with almost 50 members and approximately 20 chemokine receptors. Chemokines bind to its cell surface cognate receptors modulating biological activities and activating intracellular signaling pathways. The normal breast expresses a number of chemokines but at a very low level.

Among multiple chemokines, CXCL8, CCL2, CCL4, CCL5, and CCL18 are well-studied in breast cancer. The CXC family chemokine CXCL8 is primarily associated with cell cycle regulation as well as in angiogenesis. CXCL12-CXCR4 axis is one of the most studied ligand-receptor pairs in metastasis, where CXCR4 expression is higher in breast tumors. CXCR4 controls chemotaxis towards CXCL12, highly expressed in lung, liver, bone, and lymph nodes, which are the preferential metastatic sites of breast cancer cells. CCL2 is highly expressed in both tumor and tumor microenvironment cells, exerting its pro-tumor effects indirectly by promoting angiogenesis and enriching leukocytes infiltration. Chemokine CCL5 is involved in T helper cell recruitment, showed higher expression in multiple cell types of TME as compared to healthy tissue. CCL5 is linked to macrophage infiltration in breast cancer animal models. However, in human breast xenografts, its expression negatively correlates with macrophage recruitment implicating an indirect role of CCL5. Similarly, CCL18 promotes malignant behavior and correlates with metastasis of human breast cancer, however, a major source of CCL18 is tumor associated macrophages. CCL18 is induced by IL-4, IL-10, and IL-13, therefore, a constituent of M2-like polarized macrophages. Overall, the chemokines have been proposed as possible therapeutic targets for metastatic breast cancer. However, previous studies suggest that most of the studied chemokines are acting indirectly in breast pathogenicity.

The innovative concept of the current disclosure is the identification of CC chemokine ligand (CCL24) in association with breast cancer progression. As described above, previous studies have described the role of different chemokines in breast cancer. For example, CCL18 is secreted by the tumor associated macrophages and promotes breast cancer metastasis; CXCL12 attracts CXCR4 expressing breast cancer cells to lung, liver, bone and lymph node metastatic sites; high levels of CCL2 in breast cancer is expressed by tumor cells and correlates with macrophage infiltration.

However, humanized CCL2 neutralizing antibody is ineffective in suppressing CCL2 serum level or tumor progression due to a feedback mechanism that increases CCL2 production. Hence, there is an unmet need to develop alternate strategies. There is no study in the literature addressing any connotation, including expression and function, of CCL24 in breast cancer. It is innovative to determine the clinical significance of CCL24 as a potential biomarker of aggressive breast cancer (such as triple negative breast cancer) and its role in breast cancer development and metastasis. Successful completion of this will open a new direction to further establishing the clinical significance of CCL24 chemokine as a biomarker of aggressive breast cancer, and a novel therapeutic target in breast cancer progression and metastasis.

The current disclosure offers that the CCL24 molecule is at the interface of oncology and immunology, highly expressed in aggressive breast cancer cells and is associated with tumor promoting activities by increasing immune suppressive events in the tumor microenvironment. Therefore, the current disclosure postulates that the chemokine CCL24 drives the progression of aggressive breast cancer leading to metastasis. The rationale for this hypothesis is based on observations that the expression of CCL24 specific to basal-like breast cancer cells may serve as a selected variant evading immune system and promoting breast cancer metastasis.

High levels of chemokine ligand CCL24 is specifically expressed by aggressive breast cancer cells, and therefore, may function as a driving factor of breast cancer metastasis. CCL24 is linked with the polarization of tumor associated macrophage and promoting immune suppressor cells. Therefore, identification and characterization of a novel CCL24 chemokine associated with breast cancer progression and metastasis, directing immunosuppressive events at the tumor site will have a significant clinical impact on the development of CCL24-specific targeted therapy. If successful, potential oncogenic function of CCL24 may help to revolutionize treatment regimens eliminating mortality associated with metastatic breast cancer, and accelerate the progressive vision toward ending breast cancer.

The CCL24 molecule is unique in that: 1) it is associated with inflammation, which plays a significant role in cancer development and progression; 2) CCL24 is a chemoattractant, which attracts various immune cells types in the developing bed of neoplastic cells, supporting tumor promotion; and 3) CCL24 is highly expressed in triple negative breast cancer cells and, therefore, may promote the migration and metastasis of breast cancer.

So far, chemokine ligands studies are associated indirectly in breast cancer progression and metastasis. For example, CCL18 is secreted by the tumor associated macrophages and promotes breast cancer metastasis; CXCL12 attracts CXCR4 expressing breast cancer cells to lung, liver, bone and lymph node metastatic sites; high level of CCL2 in breast cancer is expressed by tumor cells and correlates with macrophage infiltration. However, humanized CCL2 neutralizing antibody is ineffective in suppressing CCL2 serum level or tumor progression due to feedback mechanism that increases CCL2 production. For the first time, the current disclosure proposes to determine the oncogenic function of the chemokine ligand CCL24 in breast cancer.

CCL24 in breast TME induces tumor promoting environment due to increased trafficking of CCR3 expressing immune suppressor cells. Literature suggests there are 9 known ligands (CCL5, CCL7, CCL11, CCL13, CCL15, CCL18, CCL24, CCL26, and CCL28) for CCR3 expressing immune suppressor cells. Using KM Plotter data analysis similar to CCL24, the current disclosure found that the hazard ratio (HR) of 1.87 was significantly higher for CCL24 (p=0.0053) as compared to CCL13 (p=0.14; HR=1.38), CCL26 (p=0.13; HR=1.55), and CCL28 (p=0.36; HR 1.30). The rest of the chemokine ligands (CCL5, CCL7, CCL11, CCL15, and CCL18) showed either no effect or better prognosis in breast cancer patients with increased level of expression. Additionally, multivariate analysis using KM-plotter data sets, showed a significantly poor prognosis (p=009; HR=1.85) with increased level of CCL24 after multivariable adjustment for other clinical and histopathological markers (Ki67, ESR1, and Her2) suggesting a selective association between high CCL24 and poor prognosis of breast cancer. These observations strongly support a key involvement of CCL24 specific to poor prognosis of breast cancer by inducing accumulation of immune suppressor cells promoting breast cancer metastasis.

Based on the current disclosure's preliminary studies with respect to CCL24, there are two critical observations: 1) CCL24 is highly expressed by the aggressive triple negative breast cancer cells, and therefore, may be a driving factor of breast cancer metastasis; and 2) CCL24 may function within breast cancer tumor microenvironment by polarizing tumor associated macrophages, promoting immune suppressor cells, or defecting the effector function of cytotoxic immune cells. Thus, functional characterization of a novel, breast cancer specific CCL24 chemokine modulating immunosuppressive events at the tumor site will have a significant clinical impact on the development of CCL24-specific targeted therapy in the near future.

The development and progression of tumor cells is driven by the molecular changes accumulated within the cells. These developing tumor cells are in continuous equilibrium with the immunologic targets within the tumor microenvironment, eventually evading the immune system. The current disclosure postulates that the chemokine CCL24 drives the progression of aggressive breast cancer leading to metastasis. The rationale for this hypothesis is based on strong preliminary observations that the expression of CCL24 specific to basal-like breast cancer cells may serve as a selected variant evading immune system and promoting breast cancer metastasis.

The current disclosure utilizes two specific aims to understand the oncogenic function of CCL24 in breast cancer. Aim 1: to determine the clinical significance of CCL24 in breast cancer. In this aim, the current disclosure will determine the clinical significance of a novel chemokine CCL24 protein in clinical samples using archival specimens of breast cancer tissues. The rationale for this aim is based on higher CCL24 protein/mRNA expression in triple negative cancer cells (MDA-MB231, HCC1143, MDA-MB157 and HCC70) as compared to normal or less aggressive cell lines (MCF-10A, T47D, and MCF7). Aim 2: determine the oncogenic function and therapeutic targeting of CCL24 in breast cancer cell growth and metastasis. The current disclosure will determine the oncogenic function of CCL24 in breast cancer using in vitro and in vivo methods. The current disclosure developed CCL24-knockout and CCL24-overexpressing breast cancer cell lines for in vitro studies, and their tumorigenic potential regulating immune suppressor cells of myeloid progenitors in vivo mouse models.

Chemokine CCL24 in Cancer: Studies on the role of chemokine CCL24 in cancer remain completely uncharacterized. A previous study reports an association of CCL24 with primary and metastatic tumors of colorectal origin. However, recently it is shown that CCL24 expression decreased in glandular cells with tumor progression. There is no study in the literature addressing any connotation (including expression and function) of CCL24 in breast cancer.

Figure 1:
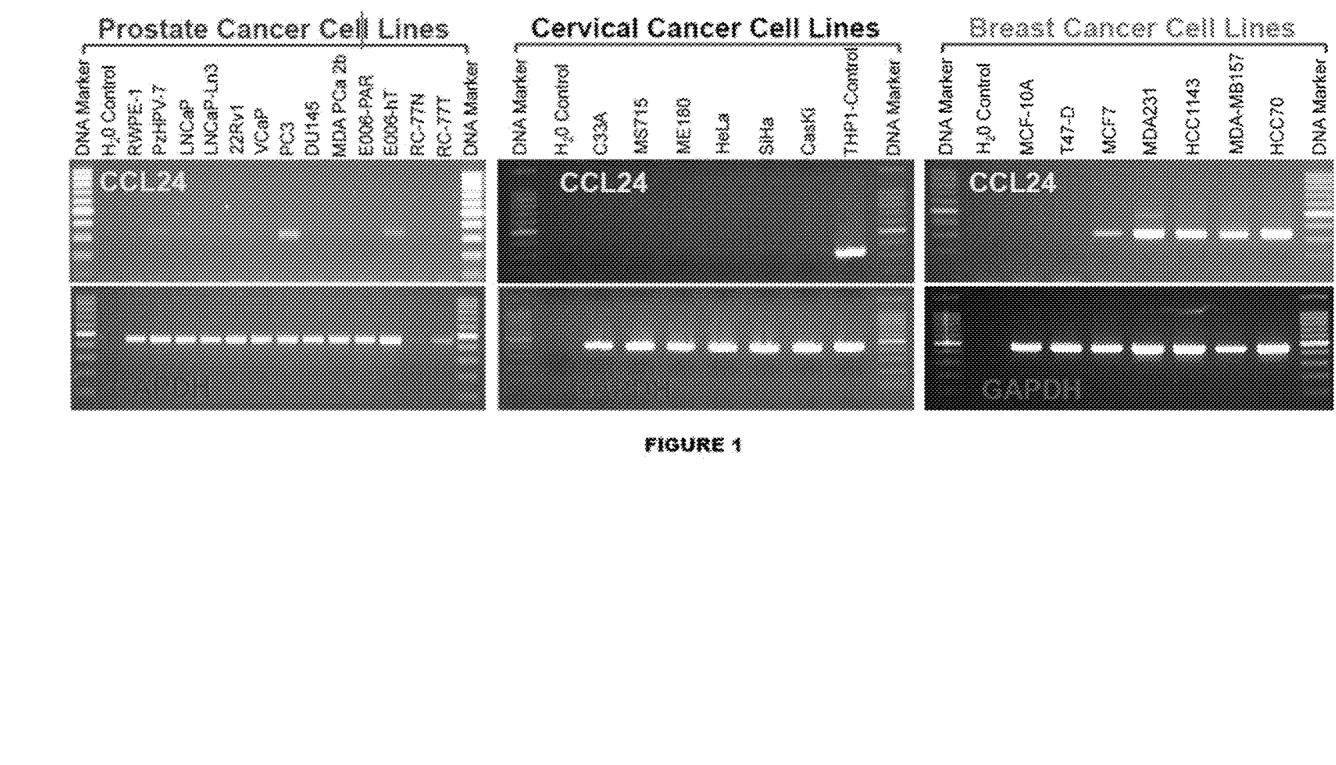
FIG. 1 shows reverse-transcriptase PCR analysis of the mRNA expression of CCL24 chemokine in Prostate, Cervical, and Breast Cancer cell lines.

Because of the inventor's prior research focus in prostate cancer, and recent interest in understanding the tumor immunology of breast and cervical cancers, the current disclosure initiated the CCL24 expression screening in a panel of human prostate, cervical, and breast cancer cell lines. In prostate cancer cell lines, it was observed a dysregulated expression of CCL24 mRNA, while no detectable mRNA was observed in cervical cancer cell lines, see FIG. 1. FIG. 1 shows reverse-transcriptase PCR analysis of the mRNA expression of CCL24 chemokine in Prostate, Cervical, and Breast Cancer cell lines. Only Breast Cancer cell lines showed a strong differential expression of CCL24 between less tumorigenic and highly aggressive TNBC cells.

However, CCL24 mRNA expression was very strong and consistent in TNBC cells (MDA-MB231, HCC1143, MDA-MB157 and HCC70) as compared to normal or less tumorigenic (MCF-10A, T47D, and MCF7) breast cancer cells (see FIG. 1). The CCL24 mRNA expression in breast cancer cell lines was further validated by quantitative-PCR (q-PCR) and ELISA on the secretion of CCL24 protein in the culture supernatants. The TNBC cancer cells showed higher expression of CCL24 both at the mRNA and protein levels, see FIG. 2, which shows validation of CCL24 expression in Breast Cancer cell lines by (A) q-PCR; (B) ELISA on cell culture supernatants.

Figure 2:
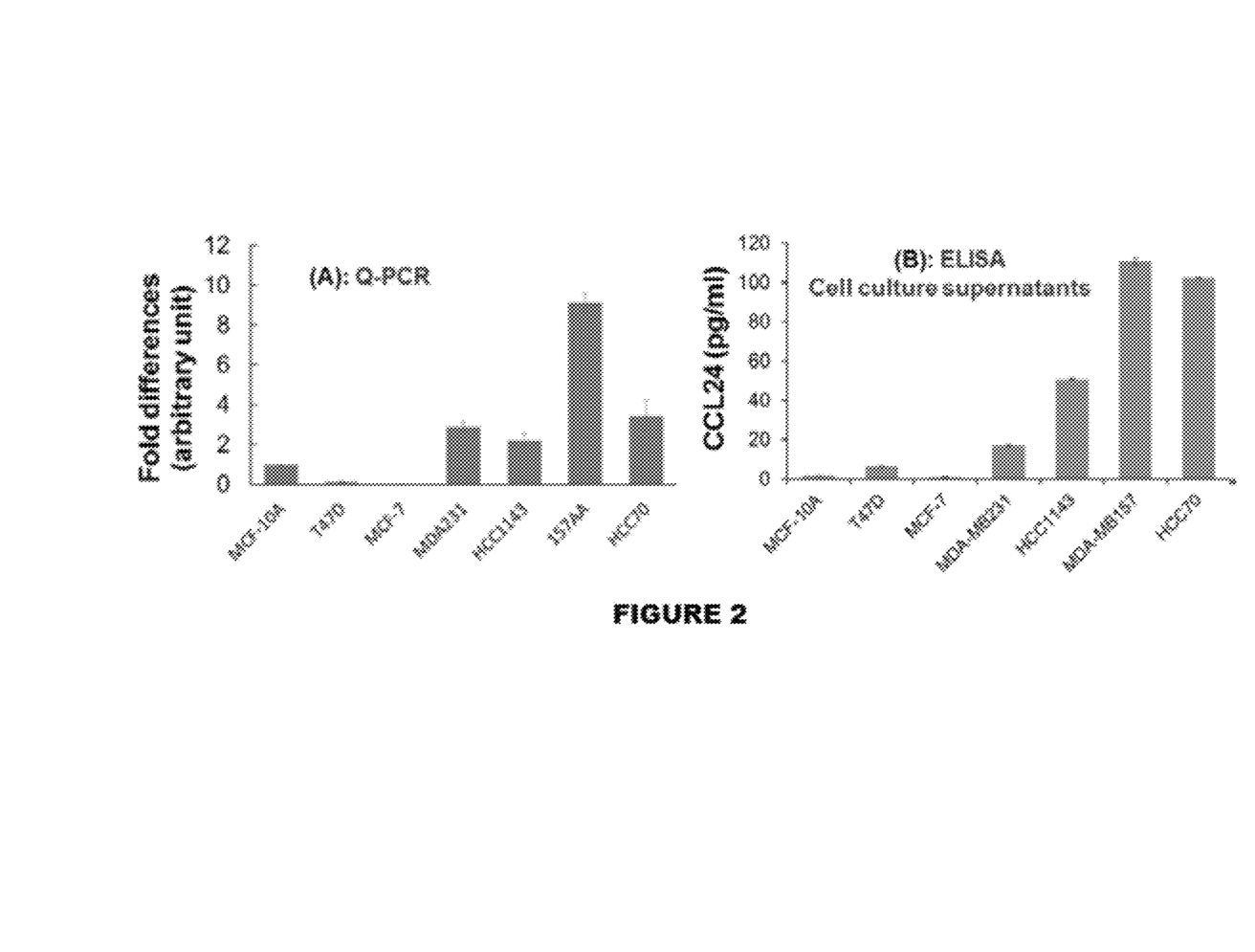
FIG. 2 shows validation of CCL24 expression in Breast Cancer cell lines by (A) quantitative-PCR (q-PCR); (B) ELISA on cell culture supernatants.
Figure 3:
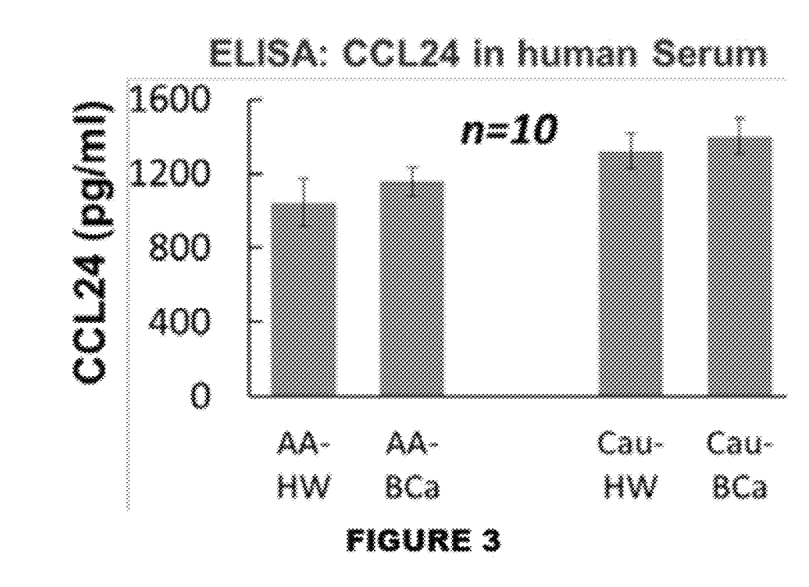
FIG. 3 shows CCL24 level in serum samples.
Figure 4:
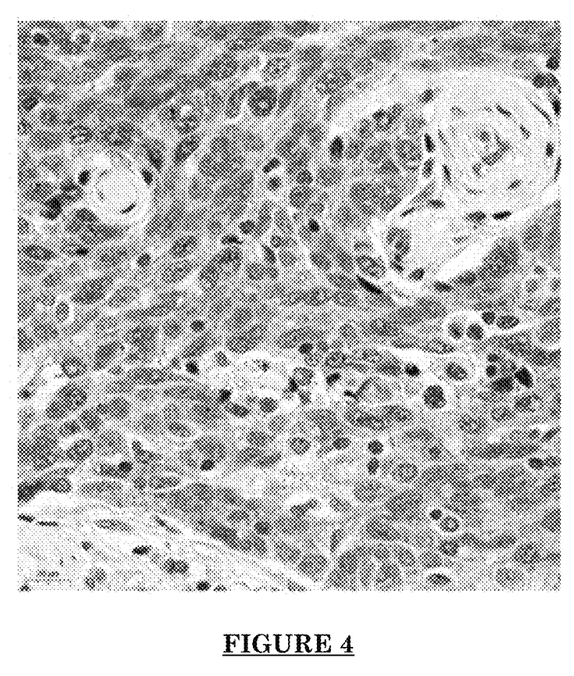
FIG. 4 shows expression of CCL24 protein in human breast cancer. IHC shows CCL24 protein staining (brown) in carcinoma cells of TNBC.
Figure 5:
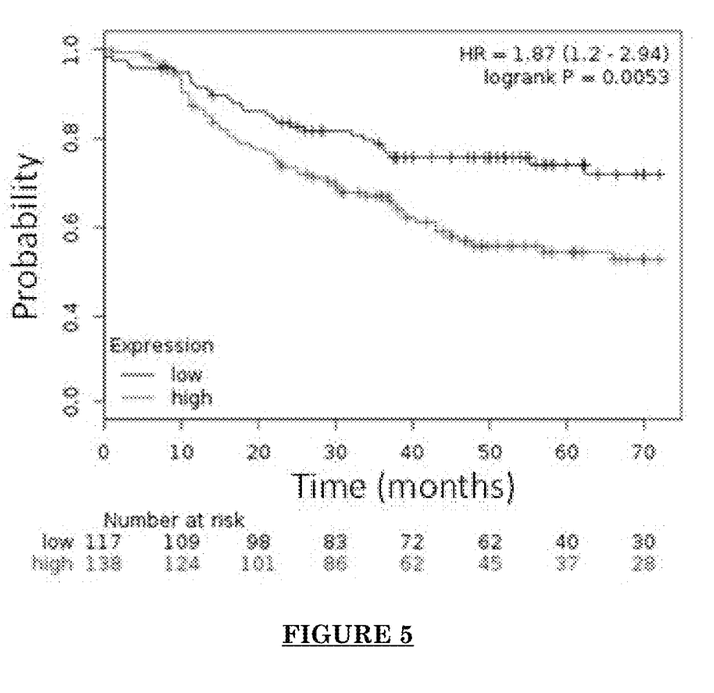
FIG. 5 shows a Kaplan-Meier Plot analyzing the correlation between CCL24 expression and survival in TNBCs (n=255).

As part of the current disclosure's research to propose CCL24 as serum-based novel biomarker due to its specificity to aggressive breast cancer, CCL24 chemokine levels in serum samples from human breast cancer patients were analyzed. Observations show a higher level of CCL24 mRNA and protein in TNBC cell lines of African American (AA) ethnicity (MDA-MB157 and HCC70) as compared to Caucasians (MDA-MB231 and HCC1143: FIGS. 1&2). The current disclosure used 10 serum samples each from healthy and breast cancer women of AA ethnicity, and healthy and breast cancer women of Caucasian origin. Surprisingly, the current disclosure did not observe any difference between healthy and cancer patients serum level of CCL24, see FIG. 3. FIG. 3 shows CCL24 level in serum samples. AA-HW: African American Healthy Women; AA-BCa: African American women with Breast Cancer; Cau-HW: Caucasian Healthy Women; Cau-BCa: Caucasian women with Breast Cancer.

These results could be due to 1) very small sample size; 2) the tested serum samples are from the primary breast cancer patients; and 3) it could be possible that the CCL24 released by the tumor cells may not be found in free-state in the circulation. Nonetheless, preliminary observations strongly support a direct role of CC chemokine ligand (CCL24) in breast cancer progression and metastasis. Therefore, the current disclosure addresses the question that CCL24 may serve as an oncogenic driver in breast cancer cells and at the same time increasing lymphocytes trafficking at the tumor site establishing pro-tumor environment stimulating breast cancer metastasis. Successful completion of this study will open a new direction in establishing the clinical significance of CCL24 as a molecular marker and a therapeutic target including immunotherapy intervening the progression and development of aggressive/metastatic breast cancer.

Understanding the molecular basis of breast cancer is important in identifying novel molecule(s) associated with the development and progression of this disease. In this aim, the current disclosure will determine the clinical significance of a novel chemokine CCL24 in breast cancer progression. Based on strong preliminary observations, the current disclosure will determine the expression of CCL24 protein in clinical samples using archival specimens of breast tumor tissues. The rationale for this study is that the CCL24 is significantly higher in TNBC (MDA-MB231, HCC1143, MDA-MB157 and HCC70) than the normal or less aggressive cell lines (MCF-10A, T47D, and MCF7).

(1.1) Collection of breast tissue samples. The current disclosure will obtain archival breast tissue samples and utilize the Core facility at Medical College of Wisconsin. The current disclosure will analyze CCL24 protein expression by quantitative immunohistochemistry (IHC) in a material of 2,000 primary invasive breast cancer specimens assembled into tissue microarrays that have been collected by Dr. Rui (Study collaborator). There is extensive clinical follow-up data on these specimens (median follow-up of 8.8 years), including histopathological variables and treatment. These data will allow us to adjust clinical outcome correlation of CCL24 in multivariable analysis to determine whether tumor expression of CCL24 is an independent predictor of clinical outcome. Dr. Rui also has a breast cancer progression tissue microarray of 40 normal, 40 DCIS, 60 invasive breast cancers (grades 1-3), and 40 lymph node metastases. This progression array will allow the examination of CCL24 expression in tumors across different phases of progression. All these human breast tissue specimens are archival materials and will be received in a blinded fashion (de-identified) and the PI does not have any access to patient's personal information, and therefore exempt from full IRB review.

(1.2) Pathological analysis of the breast tissue specimens. This is the first time the CCL24 protein will be analyzed for its clinical implications in breast cancer. IHC staining will be performed by a dedicated facility at the Clinical Pathology Core at the Medical College of Wisconsin. We have established sensitive IHC of CCL24 in formalin-fixed, paraffin-embedded tissue using a robotic Agilent/Dako Omnis autostainer. For increased sensitivity and the opportunity to measure CCL24 in both the cancer cell compartment and the stromal cell compartment of tumors, multiplexed immunofluorescence will be used. CCL24 will be detected using Cy5 channel, pan-cytokeratin staining will help identify the cancer cell compartment and distinguish it from the stromal compartment, and DAPI will stain cell nuclei blue. Stained slides will be digitized into images on the Panoramic Flash 250 scanner (3DHistech). CCL24 will be objectively quantified in cancer cells and in stromal cells using the advanced Tissue Studio platform. Correlation to clinical outcome will be performed using Kaplan-Meier analyses with log-rank statistics, followed by Cox regression for multivariable adjustment for clinic-pathological and treatment variables.

(1.3) Sample size calculation and analysis plan. The clinical outcome cohort will be randomly divided into a training and validation set. Based on preliminary analysis, we expect that in the validation cohort of 1,000 patients, 10-year progression-free survival (PFS) is 82% and the time from the surgery varies uniformly from 10 to 20 years. It is assumed that high-risk patients identified by the optimal cutoff for a biomarker will have 10-year PFS of 70% or less and at least 20% of the 600 patients are high-risk. Then, the sample size of 120 patients in the high-risk group and 480 patients in the low risk group provides 80% power to detect the hazard ratio of 1.74 using the two-sided log-rank test with alpha=0.05. If the proportion of high-risk patients is higher than 20% or 10-year PFS is lower than 70%, then the power is higher. The sample size will also effectively allow multivariable adjustment for key clinicopathological variable, including, age, race, tumor size, histological grade, lymph node status, metastasis status, hormone receptor status, and treatment. The Fisher's z-test for correlation (based Pearson's correlation coefficient) will have greater than 95% power to detect a linear association of 0.3 or greater at the 5% level of significance. Means and 95% confidence intervals will be reported for continuous variables; medians and interquartile ranges will be substituted when skewness cannot be remedied. The comparative expression of CCL24 in paired tissue samples (benign and malignant) will be done using McNemars test. Kaplan-Meier curves will be drawn to illustrate the significance of CCL24 expression with patient prognosis.

This aim is designed to examine the clinical significance of chemokine CCL24 in the development and progression of breast cancer. The study is expected to define the pattern and extent of CCL24 protein expression providing a novel insight to predict the outcome of breast cancer. Because CCL24 is a chemokine and plays a critical role in trafficking of lymphocytes, it is expected that the expression level of CCL24 protein will have clinical significance with tumor grade and stage in human breast tissue specimens. If so, this will be the very first study providing evidence to establish the clinical significance of CCL24 in the growth and development of breast cancer.

Aim 2: To determine the oncogenic function and therapeutic targeting of CCL24 in breast cancer. Preliminary studies indicate strong expression of CCL24 mRNA and protein in highly aggressive TNBC cells (MDA-MB231, HCC1143, MDA-MB157 and HCC70) in contrast to normal (MCF-10A), ER+ (T47D), and ERPR+ (MCF7) breast cancer cells. Further extension of CCL24 mRNA expression in a panel of prostate cancer cell lines showed very low to non-detectable, while in cervical cancer cell lines CCL24 mRNA was not detectable. This observation suggest a critical role of CCL24 specific to breast cancer cell growth and metastasis. Therefore, in this study, the current disclosure proposes to determine the oncogenic function of CCL24 in breast cancer using in vitro and in vivo assays.

(2.1). In vitro functional analysis of CCL24 in breast cancer. (2.1a) Establishment of a CCL24 knockout (KO)/over-expressed breast cancer cell lines: CCL24 mRNA is highly expressed in TNBC cell lines, while low to non-detectable in MCF-10A, T47D, and MCF-7 cell lines. Since the functional significance of CCL24 in breast cancer remains uncharacterized, the current disclosure will determine the gene function of the chemokine CCL24 by generating CCL24-KO cell lines of MDA-MB-231 and MDA-MB-157 using short hairpin RNA (shRNA), and over-expression of CCL24 in MCF-10A and T47D cells using CCL24 DNA plasmid. The selection of MCF-10A and T47D for over-expression or MDA-MB-231 and MDA-MB-157 for silencing of CCL24 is based on expression analysis of CCL24 as in FIG. 1. The MDA-MB-231 and MDA-MB-157 are triple negative cells representing highly aggressive and metastatic stage of breast cancer, while MCF-10A is non tumorigenic and T47D is less aggressive. The respective cell lines will be transfected with CCL24-specific shRNA to silence CCL24 activity or CCL24 cDNA plasmid for over-expression. Both the constructs, shRNA and cDNA plasmid specific to CCL24, along with their respective controls are commercially available (OriGene Technologies). Following the establishment of CCL24-KO or over-expressing breast cancer cell lines, the current disclosure will screen and test multiple clones for KO or over-expression of CCL24. Expression of CCL24 at both the mRNA and protein levels will be validated using real-time-PCR and Western blotting analysis. The transfected clones that showed at least >2-fold down- or up-regulation in CCL24 gene expression and significant reduction or enhanced cell proliferation and cell invasion assay compared to their parental (control) cell lines, will be used for in vitro and in vivo functional assays.

(2.1b) Effect of cell proliferation. The human breast cancer cell lines MCF-10A and T47D over expressing CCL24, and MDA-MB-231 and MDA-MB-157 silenced for CCL24, with their respective control cell lines, will be compared in cell proliferation assays determining the molecular function of CCL24 gene. These cell lines will be seeded into 96 well plates. A MTT assay will be performed at 24, 48, 72, and 96 hours to examine the function of CCL24 in breast cancer cell proliferation. The current disclosure will also perform cell growth kinetics of these selected clones in comparison with their parental cells at 24, 48, 72, and 96 hours by seeding $1 \times 10^6$ cells into 100 mm tissue culture petri-dish. All experiments will be conducted in triplicate, and will be repeated at least three times. Quantitative data will be collected and statistically analyzed.

(2.1c) Cell invasion assay. A Boyden chamber invasion assay with matrigel will be performed to test the oncogenic function of CCL24 in motility of the established cells. MCF-10A and T47D over expressing CCL24, and MDA-MB-231 and MDA-MB-157 silenced for CCL24 along with their respective parental cells will be seeded ($1 \times 10^4$) with 0.5 ml of the cell culture medium into inserts pre-coated with matrigel. The lower chamber of the well will be filled with complete culture medium. Following 24 and 48 hours of incubation, cells on the bottom of the membrane will be counted by staining with crystal violet. Additionally, the current disclosure will use a secondary assay, Oris™ Cell Migration Assay (Platyplus Technologies LLC, Madison, Wis.) to evaluate the function of CCL24 in cell migration. All experiments will be conducted in triplicate and will be repeated at least three times. Quantitative data will be collected and statistically analyzed.

(2.2). In vivo functional study of CCL24 in breast cancer. (2.2a) In vivo tumor growth study analyzing oncogenic function of CCL24 in breast cancer: To evaluate the oncogenic function of CCL24 gene on breast tumor cell growth, most effective clones of TNBC cells (MDA-MB-231 and MDA-MB-157) silenced for CCL24 or CCL24 over-expressing (MCF-10A and T47D) cells will be used. To establish tumors, CCL24-KO or over-expressing cells ($5 \times 10^5$) will be inoculated for subcutaneous xenograft in female nude mice (10 mice per group), which are ideal to study the gene function in tumor biology. The parental cells transfected with a scrambled shRNA or empty vector will serve as control. Tumor volume will be measured using a Vernier caliper as demonstrated in our previous studies. At the end of the experiment, tumors will be harvested and weighed. Liver and lungs will be checked for metastatic lesions. Tumors will be snap frozen, and paraffin-embedded tissue sections will be stained with hematoxylin and eosin to determine tissue histology including the extent of necrosis or apoptosis. The cell proliferation index and angiogenesis markers (Ki-67; PCNA; BrdU and VEGF) will be assessed using (IHC).

(2.2b) Analysis of immune suppressor cells polarization in the tumor microenvironment. Unarguably, tumor cells induce immune defects including mobilization of immune suppressor cells (T-regulatory cells; myeloid-derived suppressor cells: MDSCs; and polarization of macrophages) conducive to tumor promoting environment. Currently, T-regs and MDSCs are therapeutic targets to augment anti-cancer activities. Since, the events at the tumor site dictate the destruction or promotion of tumor cells; CCL24 deletion will inhibit the polarization of tumor associated macrophages (TAM) and infiltration of immune suppressor cells in the tumor microenvironment. To determine the polarization and infiltration of macrophages and MDSCs due to chemokine CCL24 in breast cancer cells, 4-6 week old female NOD-SCID mice will be injected by intraperitoneal route with human PBMCs ($1\times10^7$ PBMCs in 100 µl of PBS) from healthy donor. At the same time, 5×105 breast tumor cells (CCL24-KO or overexpressed along with respective control cell lines in 100 ul of volume) will be injected subcutaneously on back flank of NOD-SCID (10 mice per group). Tumor growth will be monitored as in Aim 2.2. At the end of the experiment, mice will be sacrificed to harvest the spleen and tumor to measure the amount of immune suppressor cells (T-regs; MDSCs; and TAM) using phenotypic markers CD4+ FoxP3+, and CD11b+ Gr1+). Liver and lungs will be checked for metastatic lesions. Excised tumors will be weighed, and divided into two parts. One part will be frozen fixed and paraffin embedded for the analysis of gross morphological changes in tumor cells. The second part of the tumor will be digested with the enzyme solution to prepare a single cell suspension. The lymphocytes will be gated using anti-CD45 antibody to analyze the level of T-regs and MDSCs and the polarization of TAM (from M1 to M2 using macrophage-specific phenotypic markers).

(2.2c) Immune suppressive cytokines analysis in tumor lysate. From the experimental settings as in Aim 2.3, tumor cell lysate will be prepared using protease and phosphatase inhibitors in PBS with subsequent vortexing and sonication. Following the protein estimation using Bradford reagent, equal amounts of protein from CCL24 KO or over-expressed cells and control tumor cell lysates will be used to perform ELISA assay for IL-10, TGF-β, TNF-α, and GMCSF.

(2.2d) Therapeutic targeting of CCL24 by antibody neutralization. Testing of the therapeutic efficacy of CCL24 targeting uses syngeneic mouse models. Mice will be inoculated subcutaneously with 4T1 or E0771 breast tumor cells respectively in Balb/c or C57BL/6 mice. For the in vivo blocking of CCL24, neutralizing antibodies diluted in PBS (CCL24 antibodies (CCL24/Eotaxin-2 MAb and CCL24/Eotaxin-2 Affinity Purified Polyclonal Ab, R&D systems) will be mixed and used at 50 µg/dose (monoclonal) and 10 µg/dose (polyclonal). Isotype controls rat IgG2A and normal goat IgG (R&D systems) will be mixed and used at a similar dose. The mice will be treated with the neutralizing antibodies 1 day before tumor cell inoculation with 4T1 or E0771 cells and then every other day post tumor inoculation for two weeks. The mice will be culled on day 21 for tumor and spleen harvesting and analyzing immune suppressor cells as above. Immune suppressor cells express CCR3, a receptor for CCL24. As proposed in this invention, higher expression of CCL24 in breast tumors will increase the accumulation of CCR3 immune suppressor cells at the tumor site promoting metastasis of breast cancer. Therefore, the proposed innovation is that targeted inhibition of CCL24-CCR3 axis will inhibit breast cancer cell growth and metastasis.

(2.2e) Statistical analysis. Mice will be randomly assigned to one of two groups (CCL24-KO or control, with injection of different tumor cell lines). Ten mice per group results in an overall sample size of 40 mice per experimental set (2 cell lines with their respective controls). One goal is to measure tumor growth and metastasis. Since the current disclosure postulates that the mice with silenced CCL24 function will either show similar (H0) or significantly less (H1) tumor growth than control mice, a one-sided two-sample t-test will be used to make inferences about differences in mean tumor weight and volume. With 10 mice per group, the t-test will have greater than 95% power to detect a difference equivalent to 2.0 standard deviations in the two groups at the 5% level of significance. Ten mice per group will also ensure detection of a difference as small as 1.2 standard deviations with sufficient (83%) power. Should the data not meet the assumptions of the t-test; appropriate transformations will first be attempted. If one cannot be found, the nonparametric Wilcoxon (Mann-Whitney) Rank-Sum test will be used instead; and this should result in no greater than a 5% loss of power for the test of our primary outcome.

Expected outcomes and alternative strategies. By completing the proposed experiments in this Aim, the current disclosure expects to determine the novel function of CCL24 in breast tumor cell growth, and that the inhibition of CCL24 significantly suppresses invasion and migration of breast cancer cells metastasis compare to parental cell lines. It is expected that the knockdown of CCL24 will inhibit the modulation of immunosuppressor cells (infiltration in the tumor and macrophage polarization) in breast tumor microenvironment, thereby inhibiting migration and metastasis of breast cancer cells supporting our proposed hypothesis. The current disclosure proposes that diminished immunosuppressive activity following therapeutic targeting of CCL24 will apply breaks on the evolution of metastatic behavior of breast tumor cells providing a novel opportunity for an improved management/treatment of breast cancer. Since immune suppressor cells (T-regs, MDSCs and macrophages) express CCL24 receptor CCR3, neutralization of CCL24 is expected to inhibit immune suppressor cells trafficking in to TME.

```
SEQUENCE LISTING
<110> University of South Carolina
<120>CCL24 as a Diagnostic and Therapeutic Target for Breast Cancer
<130>2033101.0000139
<140>Unknown
<141>2020 NOV. 25
<150>U.S. Provisional Application No. 62/940,396
<151>2019 NOV. 26
<160>2
<170>PatentIn
<210>1
<211>1441
<212>DNA
<213>Homo sapiens
<221>CDS
<222>111 . . . 470
<400>1
ATCATTTCTG CTCTGCACTT GGCACCAAGG CTGTCACCCT GTTACCTCCG GGTCCTTTCC      60

TCCTGCACGT CAGCTTTGAG CCCCGAGCTG GTGCTTCTGC TCTCTGAGAC ATGGCAGGCC    120
```

```
TGATGACCAT AGTAACCAGC CTTCTGTTCC TTGGTGTCTG TGCCCACCAC ATCATCCCTA    180

CGGGCTCTGT GGTCATCCCC TCTCCCTGCT GCATGTTCTT TGTTTCCAAG AGAATTCCTG    240

AGAACCGAGT GGTCAGCTAC CAGCTGTCCA GCAGGAGCAC ATGCCTCAAG GCAGGAGTGA    300

TCTTCACCAC CAAGAAGGGC CAGCAGTTCT GTGGCGACCC CAAGCAGGAG TGGGTCCAGA    360

GGTACATGAA GAACCTGGAC GCCAAGCAGA AGAAGGCTTC CCCTAGGGCC AGGGCAGTGG    420

CTGTCAAGGG CCCTGTCCAG AGATATCCTG GCAACCAAAC CACCTGCTAA TCCCCGCCCA    480

GCCCTCCAGC CCTGAGTTTG GGCCTGAGCT GCTTGGCGGG CTACTCGGGG CCTGGAGAAG    540

CCACAGTGAT GGGGGGAAGA GCTAATTTTC CTGTTTCTTA GCAACACTCT CCAGGGATGT    600

GTCTCTTCTA TGAAAAACCC GAGGGAGCAG GTGATGTGGT TCCCGGGGGC TGAGCAATGG    660

CTCCAAGCAT CCAAGGCCCC TTGCCTTTCT GGAGCTGGGT GAGAAGATCC CAGAAGGAGA    720

GCAGTGGCAA CTCTTTGCCT TCTCCTCCTG ACCTGGTTCT GATGCTTTTT CTTTTTTTTT    780

TTTTTCTGAG ACGGAGTCTC GCTCTGTCAC CCAGGCTGGA GTGCAGTGGC ACAATCTCGG    840

TTCACTGCAA CCTCCGCCTC CTGGGTTCAA GTGATTCTCG TGCCTCAGCC TCCCGAGTAC    900

CTGGGACTAC AGGTGTGTAC CACCACACCC AACTAACTTT TGTATTTTTA GTAGAGATGA    960

GGTTTCACCA TGTTGGCCAG GCTGGTCTCA AACTCCTGGC CTCAAGTGAT CTACCTGCCT   1020

CGGCCTCCCA AAGTGCTGGG ATTACAGGCA TGAGCCACCA CACCCAGCCT ACTCAAACTT   1080

TTATGTTGAA AAAAAAAAT CATAATTTTT TTTTTTTAA AGGAAATGAA CGTGGAGGAC    1140

TGGGGTGAAG GGCCAGCCTG GGTAGTTTAA TCTTTTTGGG AAGACATGAC TTTAAGGAGA   1200

TTCCCTGCTT TGTGACAGGT TGCTCCATGC TGTCTTGGGG ACAAGGGCCT GTACTGCCTT   1260

CAAATCTGGG CTCACCCCAC ATTTTGGTGA GGGGAAGATA GGGTGGGGGG ATTAGGGGA    1320

GAAAAGACTC TAGCTTTTTT TTTCTATGCA TGATATACTG TGTGGGTTTA TCAAGAGTGT   1380

AGACACAGTT GCTGTTCTCA AATAATAGGC CAAATAAAAT GCGATTCTTT TTTTCTTTGA   1440

A
<210>2
<211>119
<212>PRT
<213>Homo sapiens
<400> 2
Met Ala Gly Leu Met Thr Ile Val Thr Ser Leu Leu Phe Leu Gly Val
             5                  10                  15

Cys Ala His His Ile Ile Pro Thr Gly Ser Val Val Ile Pro Ser Pro
            20                  25                  30

Cys Cys Met Phe Phe Val Ser Lys Arg Ile Pro Glu Asn Arg Val Val
        35                  40                  45

Ser Tyr Gln Leu Ser Ser Arg Ser Thr Cys Leu Lys Ala Gly Val Ile
    50                  55                  60

Phe Thr Thr Lys Lys Gly Gln Gln Phe Cys Gly Asp Pro Lys Gln Glu
65                  70                  75                  80

Trp Val Gln Arg Tyr Met Lys Asn Leu Asp Ala Lys Gln Lys Lys Ala
                85                  90                  95

Ser Pro Arg Ala Arg Ala Val Ala Val Lys Gly Pro Val Gln Arg Tyr
            100                 105                 110

Pro Gly Asn Gln Thr Thr Cyc
            115
```

Various modifications and variations of the described methods, pharmaceutical compositions, and kits of the disclosure will be apparent to those skilled in the art without departing from the scope and spirit of the disclosure. Although the disclosure has been described in connection with specific embodiments, it will be understood that it is capable of further modifications and that the disclosure as claimed should not be unduly limited to such specific embodiments. Indeed, various modifications of the described modes for carrying out the disclosure that are obvious to those skilled in the art are intended to be within the scope of the disclosure. This application is intended to cover any variations, uses, or adaptations of the disclosure following, in general, the principles of the disclosure and including such departures from the present disclosure come within known customary practice within the art to which the disclosure pertains and may be applied to the essential features herein before set forth.

SEQUENCE LISTING

<160> NUMBER OF SEQ ID NOS: 2

<210> SEQ ID NO 1
<211> LENGTH: 1441
<212> TYPE: DNA
<213> ORGANISM: Homo sapiens

<400> SEQUENCE: 1

```
atcatttctg ctctgcactt ggcaccaagg ctgtcaccct gttacctccg ggtcctttcc      60
tcctgcacgt cagctttgag ccccgagctg gtgcttctgc tctctgagac atggcaggcc     120
tgatgaccat agtaaccagc cttctgttcc ttggtgtctg tgcccaccac atcatcccta     180
cgggctctgt ggtcatcccc tctccctgct gcatgttctt tgtttccaag agaattcctg     240
agaaccgagt ggtcagctac cagctgtcca gcaggagcac atgcctcaag gcaggagtga     300
tcttcaccac caagaagggc cagcagttct gtggcgaccc aagcaggag tgggtccaga     360
ggtacatgaa gaacctggac gccaagcaga gaaggcttc ccctagggcc agggcagtgg     420
ctgtcaaggg ccctgtccag agatatcctg gcaaccaaac cacctgctaa tccccgccca     480
gccctccagc cctgagtttg ggcctgagct gcttggcggg ctactcgggg cctggagaag     540
ccacagtgat gggggggaaga gctaattttc ctgtttctta gcaacactct ccagggatgt     600
gtctcttcta tgaaaaaccc gagggagcag gtgatgtggt tccgggggc tgagcaatgg     660
ctccaagcat ccaaggcccc ttgcctttct ggagctgggg gagaagatcc cagaaggaga     720
gcagtggcaa ctctttgcct tctcctcctg acctggttct gatgcttttt ctttttttt      780
tttttctgag acggagtctc gctctgtcac ccaggctgga gtgcagtggc acaatctcgg     840
ttcactgcaa cctccgcctc ctgggttcaa gtgattctcg tgcctcagcc tcccgagtac     900
ctgggactac aggtgtgtac caccacaccc aactaacttt tgtatttta gtagagatga     960
ggtttcacca tgttggccag gctggtctca aactcctggc ctcaagtgat ctacctgcct    1020
cggcctccca aagtgctggg attacaggca tgagccacca cacccagcct actcaaactt    1080
ttatgttgaa aaaaaaaat cataatttt tttttttaa aggaaatgaa cgtggaggac    1140
tggggtgaag ggccagcctg ggtagtttaa tcttttggg aagacatgac tttaaggaga    1200
ttccctgctt tgtgacaggt tgctccatgc tgtcttgggg acaagggcct gtactgcctt    1260
caaatctggg ctcaccccac attttggtga ggggaagata gggtgggggg attagggga    1320
gaaaagactc tagcttttt tttctatgca tgatatactg tgtgggttta tcaagagtgt    1380
agacacagtt gctgttctca aataataggc caaataaaat gcgattcttt ttttctttga    1440
a                                                                     1441
```

<210> SEQ ID NO 2
<211> LENGTH: 119
<212> TYPE: PRT
<213> ORGANISM: Homo sapiens

<400> SEQUENCE: 2

```
Met Ala Gly Leu Met Thr Ile Val Thr Ser Leu Leu Phe Leu Gly Val
1               5                   10                  15

Cys Ala His His Ile Ile Pro Thr Gly Ser Val Val Ile Pro Ser Pro
            20                  25                  30
```

-continued

```
Cys Cys Met Phe Phe Val Ser Lys Arg Ile Pro Glu Asn Arg Val Val
        35                  40                  45

Ser Tyr Gln Leu Ser Ser Arg Ser Thr Cys Leu Lys Ala Gly Val Ile
    50                  55                  60

Phe Thr Thr Lys Lys Gly Gln Gln Phe Cys Gly Asp Pro Lys Gln Glu
65                  70                  75                  80

Trp Val Gln Arg Tyr Met Lys Asn Leu Asp Ala Lys Gln Lys Lys Ala
                85                  90                  95

Ser Pro Arg Ala Arg Ala Val Ala Val Lys Gly Pro Val Gln Arg Tyr
            100                 105                 110

Pro Gly Asn Gln Thr Thr Cys
            115
```

What is claimed is:

1. An immunohistochemistry method comprising:
   examining a subject, via obtaining at least one breast cell tissue sample, to detect the presence of a tumor microenvironment;
   employing immunohistochemistry staining of the at least one breast cell tissue sample to identify at least one cancer cell compartment in the at least one breast cell tissue sample;
   measuring for a differential expression of CC Chemokine Ligand 24 ("CCL24") in the tumor microenvironment of the at least one breast cell tissue sample to differentiate between at least one non-Triple Negative tumorigenic cell and at least one Triple Negative Breast Cancer cell;
   measuring lymphocyte tracking events in the tumor microenvironment via gating at least one lymphocyte via employing at least one anti-CD45 antibody to analyze a level of at least one T-regulatory cell and at least one myeloid-derived suppressor cells; and
   measuring the amount of CCL24 in the tumor microenvironment via multiplexed immunofluorescence to determine if the subject is positive for at least one Triple Negative Breast Cancer cell.

2. The method of claim 1, wherein the CCL24 comprises the amino acid sequence of SEQ ID NO: 1.

3. The method of claim 1, further comprising measuring for a differential expression in basal-like breast cancer cells.

4. The method of claim 1, further comprising measuring for polarization of at least one tumor associated macrophage.

5. The method of claim 1, further comprising screening the tumor microenvironment for immune suppressor cells.

6. The method of claim 5, wherein the immune suppressor cells comprise CC Chemokine Receptor 3 ("CCR3") expressing immune suppressor cells.

7. The method of claim 1, further comprising measuring for defecting of effector function for cytotoxic immune cells.

8. A An immunohistochemistry method comprising:
   examining a subject to detect the presence of a tumor microenvironment via obtaining at least one breast cell tissue sample;
   employing immunohistochemistry staining of the at least one breast cell tissue sample to identify at least one cancer cell compartment in the at least one breast cell tissue sample;
   measuring for a differential expression of serum-based biomarker CC Chemokine Ligand 24 ("CCL24") in the tumor microenvironment of the at least one breast cell tissue sample to differentiate between at least one non-Triple Negative tumorigenic cell and at least one Triple Negative Breast Cancer cell; and
   measuring the amount of CCL24 in the tumor microenvironment via multiplexed immunofluorescence to determine if the subject is positive for at least one Triple Negative Breast Cancer cell.

9. The method of claim 8, wherein the CCL24 comprises the amino acid sequence of SEQ ID NO: 1.

10. The method of claim 8, further comprising measuring for polarization of at least one tumor associated macrophage.

11. The method of claim 8, further comprising screening the tumor microenvironment for immune suppressor cells.

12. The method of claim 11, wherein the immune suppressor cells comprise CCR3 expressing immune suppressor cells.

13. The method of claim 8, further comprising measuring for defecting of effector function for cytotoxic immune cells.

* * * * *